(12) United States Patent
Harand et al.

(10) Patent No.: US 7,892,209 B2
(45) Date of Patent: Feb. 22, 2011

(54) ARRANGEMENT COMPRISING A CATHETER AND CONNECTOR PIECE, AND VALVE FOR PASSAGE OF A CATHETER

(75) Inventors: Ralf Harand, Reichenau (DE); Thomas Hottkowitz, Steiβlingen (DE); Christel Wijers, Schaffhausen (NL); Reinhold Wolkenstörfer, Neunkirchen (DE); Catherine Rochat, Lussy-sur-Morges (CH); Phillipe Brosy, Botterens (CH)

(73) Assignee: NYCOMED GmbH, Konstanz (DE)

( * ) Notice: Subject to any disclaimer, the term of this patent is extended or adjusted under 35 U.S.C. 154(b) by 352 days.

(21) Appl. No.: 11/886,786

(22) PCT Filed: Mar. 28, 2006

(86) PCT No.: PCT/EP2006/061096

§ 371 (c)(1),
(2), (4) Date: Nov. 8, 2007

(87) PCT Pub. No.: WO2006/103233

PCT Pub. Date: Oct. 5, 2006

(65) Prior Publication Data

US 2008/0185006 A1    Aug. 7, 2008

(30) Foreign Application Priority Data

Mar. 31, 2005   (DE) .................. 10 2005 014 650

(51) Int. Cl.
*A61M 5/178* (2006.01)
(52) U.S. Cl. .................................. 604/167.01
(58) Field of Classification Search ............... None
See application file for complete search history.

(56) References Cited

U.S. PATENT DOCUMENTS

| 5,333,606 | A | * | 8/1994 | Schneider et al. ...... 128/200.24 |
| 5,456,284 | A | * | 10/1995 | Ryan et al. .................. 137/522 |
| 6,439,541 | B1 | * | 8/2002 | Nosel et al. .............. 251/149.1 |
| 6,575,944 | B1 | | 6/2003 | McNary et al. |

FOREIGN PATENT DOCUMENTS

WO     95/32992 A1    12/1995

* cited by examiner

*Primary Examiner* — Nicholas D Lucchesi
*Assistant Examiner* — Pritesh Patel
(74) *Attorney, Agent, or Firm* — The Nath Law Group; Sheldon M. McGee; Robert T. Burns

(57) ABSTRACT

To provide an access route which is leaktight and at the same time permits mobility and exact positioning of an instillation catheter (6), an arrangement comprising an instillation catheter (6) and a connector piece (1) for attachment to a tracheal or endotracheal tube is proposed. The connector piece (1) has a distal end (1a) for attachment to the tube, and a proximal end (1b) for attachment to a ventilation and/or suction device and comprises a branch (5) which serves for insertion of the catheter (6) and in which a valve (2) is arranged. The valve (2) is made, at least in some areas, from an elastically deformable material and can be opened by insertion of the catheter (6). The valve further comprises a proximal through-opening (21) whose inner wall has a means allowing sealing against axial flow of fluid between catheter (6) and inner wall, and, in the distal direction from the through-opening, it has a beak section (22) which, at its beak tip (23), has a normally closed slit (24).

20 Claims, 6 Drawing Sheets

ARRANGEMENT COMPRISING A CATHETER AND CONNECTOR PIECE, AND VALVE FOR PASSAGE OF A CATHETER

This application was filed under 35 U.S.C. 371 as a national stage of PCT/EP2006/061096, filed Mar. 28, 2006.

FIELD OF THE INVENTION

The present invention relates to an arrangement for delivering pharmaceutical preparations and other liquids to the lungs of a patent, and in particular to an arrangement comprising a catheter and connector piece for instilling finely dispersed lung surfactant preparations into the lungs, and a valve for passage of a catheter, in particular for reception in a connector piece. The arrangement can be attached to a tracheal or endotracheal tube.

PRIOR ART

In the clinical sector, tracheal or endotracheal tubes are often used to assist a patient's breathing. These tubes in most cases contain, in addition to ventilation devices, also suction devices for removing mucus and other liquids which may accumulate in the trachea and in the bronchi of the patient. Both these devices are attached to an (endo)tracheal tube by way of a suitable connector piece.

It may additionally be necessary to treat the lungs with medication, e.g. in the case of lung injuries, or it may be desirable to administer medicaments into the airways. The treatment and/or administration of the medicament can be made directly into the lungs. Because of their better uptake, suitable medicaments are, in particular, finely dispersed lung surfactant preparations such as are described, for example, in WO 95/032992, to which express reference is hereby made.

To ensure that the delivery of the medicaments into the lungs is as problem-free as possible in respect of the patient, and to ensure that the patient's condition is not adversely affected, removable instillation catheters are introduced directly into the endotracheal tube via a connector piece and brought to the desired position inside the lungs. It is therefore not necessary to remove the tubes, the ventilation device or the suction device. On its jacket surface, the catheter can be provided with markings which permit monitoring of its depth of insertion into the airways. In addition, radiopaque markers can be positioned on the jacket surface near the tip of the catheter and permit very precise positioning under X-ray imaging.

A connector piece permitting attachment of suction device, ventilation device and catheter to an endotracheal tube is described in U.S. Pat. No. 6,575,944.

In a connector piece of the generic type, it is important to secure the catheter in such a way that no liquid can escape from the connector piece past the catheter. In addition, after the desired position has been reached, the catheter has to be fixed so that it does not slip. This is done, for example, using a cap provided with a thread which, when screwed onto the connector piece, secures the catheter by means of clamping jaws. The abovementioned sealing is in most cases obtained by using a one-way valve, e.g. what is called a duckbill valve, which is closed under normal circumstances, i.e. with the catheter removed, and which opens when the catheter is inserted, permits introduction thereof and at the same time is intended to tightly seal the catheter. However, in the valves used in the prior art, problems occur in view of the fact that, in order to ensure an adequate seal, the valve has to enclose the catheter very tightly, but this impedes the mobility of the catheter, leads to greater force being exerted upon insertion into the tube, and therefore makes exact positioning of the catheter more difficult and increases the risk of injury. On the other hand, too loose a hold of the tube can lead to undesired escape of liquid and/or ventilation gas, especially as ventilation is in most cases performed under positive end-expiratory pressure.

DISCLOSURE OF THE INVENTION

The object of the present invention is, therefore, to permit an access route which is leaktight and which at the same time permits mobility and exact positioning of the catheter.

This object is achieved by an arrangement comprising an instillation catheter and an associated connector piece having the features of Claim 1, and by a valve having the features of Claim 6. Advantageous embodiments are set forth in the dependent claims.

The arrangement according to the invention comprising an instillation catheter and an associated connector piece can be attached to an (endo)tracheal tube. The valve serves for the passage of an instillation catheter, can be inserted into the connector piece and closes the catheter access route tightly when no catheter is inserted. Upon insertion of a catheter, it is guaranteed that the stream of fluid between the catheter's outer wall and the valve opening is minimized.

The arrangement according to the invention thus comprises an instillation catheter and a connector piece, in which the connector piece has a distal end for attachment to a tracheal or endotracheal tube and a proximal end for attachment to a ventilation and/or suction device. The connector piece further comprises a branch which serves for insertion of the catheter and in which a valve is arranged in a receiving seat. The valve has an elastically deformable material and can be opened by insertion of the catheter. The valve further comprises a proximal through-opening whose inner wall has a means for sealing against axial flow of fluid between catheter and inner wall, and, in the distal direction from the through-opening, a beak section which, at its beak tip, has a normally closed slit. The design with the beak tip, and the position of the valve fitted into the connector piece such that the catheter can be inserted from the direction of the branch, ensures that, when the catheter tube is removed, the slit of the beak tip is pressed together by internal overpressure of the ventilation and/or suction device. The catheter can thus be inserted through the through-opening of the valve into the connector piece and then opens the valve, after which it passes farther through the branch into the connector piece and via the tube to the desired position in the lungs. The sealing means on the inner wall prevents a situation where liquids or gases (e.g. ventilation gases) charged with medicaments can escape past the catheter and where, as a result, the desired dose of medicament is not administered to the patient. It thus also prevents undesired entry of microorganisms into the respiratory organs. The catheter is enclosed by the sealing means such that the catheter still remains easily movable and positionable. By contrast, in the state with no instillation catheter inserted (normal state of the valve), the closed slit at the beak tip of the valve prevents the passage of liquids or gases.

Between a connection cap, provided at the distal end of the catheter for attachment to the branch, and a connection cap provided at the proximal end area of the catheter, said catheter particularly preferably has a protective film enveloping the catheter. This prevents, on the one hand, the entry of microorganisms in the vicinity of the connection caps and, on the other hand, permits sterile handling of the catheter, since the latter can be guided by hand via the protective film. In a further preferred embodiment, the instillation catheter and/or the connector piece will be fitted with removable protection caps on every end of the liquid and/or gas pathway in order to prevent contamination or entry of microorganisms during packaging, wrapping, transport, unwrapping and handling. The protection caps will be preferably removed shortly before final use.

Likewise, the catheter preferably has, along its length, markings which show the user the position of the distal end of the catheter relative to the tube. This permits exact positioning of the catheter and, therefore, a targeted local administration of medicaments into the lungs. In a further preferred embodiment, said markings will be readable from all sides of the catheter. In a further preferred embodiment, the connector piece will have means for reading out the exact position of the catheter, including but limited to a flag window, based on transparent material that will allow a visual read out of the markings of the catheter.

The catheter preferably also has a radiopaque indicator near the distal end, additionally allowing the position of the catheter in the patient's body to be visually monitored by X-ray imaging.

The branch present on the connector piece forms an angle of between 20° and 70°, preferred between 25° and 55°, more preferred between 35° and 45° with a longitudinal axis passing through the distal end of the connector piece. This facilitates insertion of the catheter in the distal direction.

The valve according to the invention, which has an elastic material, comprises a proximal through-opening whose inner wall has a means allowing sealing relative against axial flow of fluid between catheter and inner wall, and, in the distal direction from the through-opening, the valve has a beak section which, at its beak tip, has a normally dosed slit. A catheter can be inserted through the through-opening, and the catheter then opens the valve. At the same time, the sealing means on the inner wall prevents liquids or gases with medicaments from being able to escape past the catheter and thus also prevents undesired entry of microorganisms. The catheter is enclosed by the sealing means such that the catheter still remains easily movable and positionable. With no catheter inserted, the restoring forces of the elastic material close the slit (normal state of the valve). The closed slit prevents passage of liquids or gases at the beak tip of the valve. The slit is designed, for example, such that the opposite long sides bear tightly on one another in the normal state. The sealing action can in this case be supported by suitable choice of material, for example silicone.

In the arrangement according to the invention and in the valve according to the invention, the internal diameter defined by the sealing means is advantageously between 0.05 mm and 0.2 mm, preferably between 0.1 mm and 0.15 mm smaller than the external diameter of the catheter. The exact figure depends on the desired fit between the material pairing and the absolute size. The most reliable function has been found to be in the narrower range. In this way, when the catheter is inserted into and through the valve, the sealing means exert, on the outer wall of the catheter, a pressure which permits gas-tight and water-tight enclosure. However, by choosing the fit within the stated ranges, this pressure is not too high and it further affords the catheter a good sliding mobility which is essential for the latter's positioning and additionally prevents abrupt movements of the catheter (stick-slip effect) which can lead to injuries to the patient's airways.

The through-opening in the arrangement according to the invention and of the valve according to the invention preferably comprises an outer wall with a flange which serves as a sealing abutment for positioning the valve in the receiving seat of the branch. The exact positioning and sealing achieved by these means are advantageous, because they support the function of the inner wall and of the beak tip. The abutment additionally permits a structurally simple configuration of the corresponding receiving seat in the branch.

The flange preferably has a section defined by lateral flats, the flats intersecting at the centre of the section, the centre being rounded, and each flat forming an angle of 6° with a tangent line which is parallel to the slit in the beak opening and lies at the centre of the section. With the aid of this section, an exact rotatory positioning of the valve in the receiving seat can be achieved such that, for example, the beak tip in its longitudinal extent can be adapted to the extent of a possible curvature of the inserted installation catheter.

It is also particularly advantageous if the sealing means of the arrangement according to the invention and of the valve according to the invention comprises a sealing lip which, in addition, is preferably arranged in the circumferential direction on the inner wall. It has been found that a sealing lip, while being easy to produce, also provides a particularly effective seal around the catheter and thus ensures increased safety against escape of fluids or medicaments and against entry of microorganisms.

In the arrangement according to the invention and in the valve according to the invention, it is particularly advantageous if the sealing means comprises two sealing lips which are preferably arranged in the circumferential direction on the inner wall. In this way, the advantages mentioned in the previous paragraph can be still better exploited. In addition, the second sealing lip affords added protection if the first sealing lip has been damaged, for example by the external action of an object or by previous careless handling.

Preferably, the sealing lip or sealing lips has/have a substantially bell-shaped cross section, with a radius of curvature. Upon insertion of a catheter, this shape is able to deform in order to ensure a low sliding friction while affording a good seal.

In this context, it is particularly advantageous if the radius of curvature of the sealing lip or sealing lips is at most 0.25 mm. It has been found that this value keeps the sliding friction sufficiently low while providing an excellent seal.

In the case of two or more sealing lips, a "valley" is formed in the connection area between the lips, and it too has a radius of curvature. This curvature is naturally the reverse of the curvature of the apex of the sealing lip. Particularly preferably, the radius of curvature of a connection area between the sealing lips is at most 0.1 mm. This ensures that the lips do not lie too far apart.

In the distal direction, the lip again meets the inner wall profile of the valve. In the arrangement according to the invention and in the valve according to the invention, the radius of curvature of that part of the lip extending towards the beak section and lying nearest to the beak section is at most 0.3 mm. In this way too, the effective width of the lip is limited and, consequently, excessive friction during passage of the catheter is limited. The rolling process mentioned above is simplified.

Starting from a cylindrical basic shape, the beak section of the arrangement according to the invention and of the valve according to the invention preferably narrows in a wedge formation via flats lying opposite one another. This shape of the beak section permits easy opening of the valve through pressing out of the opposite flats during insertion of the catheter. Closure when the valve moves back is also made more reliable.

Particularly preferably, the angle between the longitudinal axis of the valve and each of the two flats of the beak section is between approximately 26° and 28°. This value has proven the most suitable value in respect of easy opening and satisfactory sealing in the closed state. Minor deviations above or below this are not prejudicial.

In a preferred embodiment of the arrangement according to the invention and of the valve according to the invention, the valve is fixed by an annular cover in the receiving seat of the branch. This cover permits quick and simple insertion and exchange of the valve which, as a disposable valve, is replaced after each use, and secure fixing. The annular cover here interacts with the flange on the outside of the valve.

Finally, it is particularly preferable if the receiving seat has a snap-fit lip for snapping the annular lid securely in place. This ensures that the cover does not accidentally fall out, permits reliable fixing and sealing, and provides a tactile and also acoustic indication that the annular cover has reached its prescribed position.

In a further preferred embodiment, a one-way valve will be additionally incorporated within the liquid pathway in order to further prevent or minimize pressure lost and/or to prevent or minimize backflow of liquid fluids. The one-way valve might be incorporated anywhere within or at the end of the liquid pathway of the catheter, preferred within the cathteter or directly connected to the injection part (6a of FIG. 3a) of the catheter.

In a further preferred embodiment, the connector piece comprises additionally to the flange used for connecting the cathter a further flange useable for connecting further devices, for example a suction device. In a preferred embodiment, which is shown in FIG. 5, the flange to be connected to a suction device is in principle identical to the flange useable for connoting the catheter.

In a further preferred embodiment, the connector piece will comprise means for guiding the devices, such as the instillation catheter and/or a suction cathter towards the distal end of the connector piece 1a. In a preferred embodiment such means for guiding will be guiding lips as exemplified in FIG. 4 (11a and/or 11b) for a connector piece with one flange for an instillation catheter and in FIG. 6 for a connector piece with two flanges, one flange for an instillation catheter (11a and/or 11b) and one flange for an e.g. suction cathteter (11a' and 11b').

BRIEF DESCRIPTION OF THE DRAWINGS

The invention is explained below on the basis of an illustrative embodiment according to FIGS. 1 to 6.

EMBODIMENT OF THE INVENTION

Figure 1:
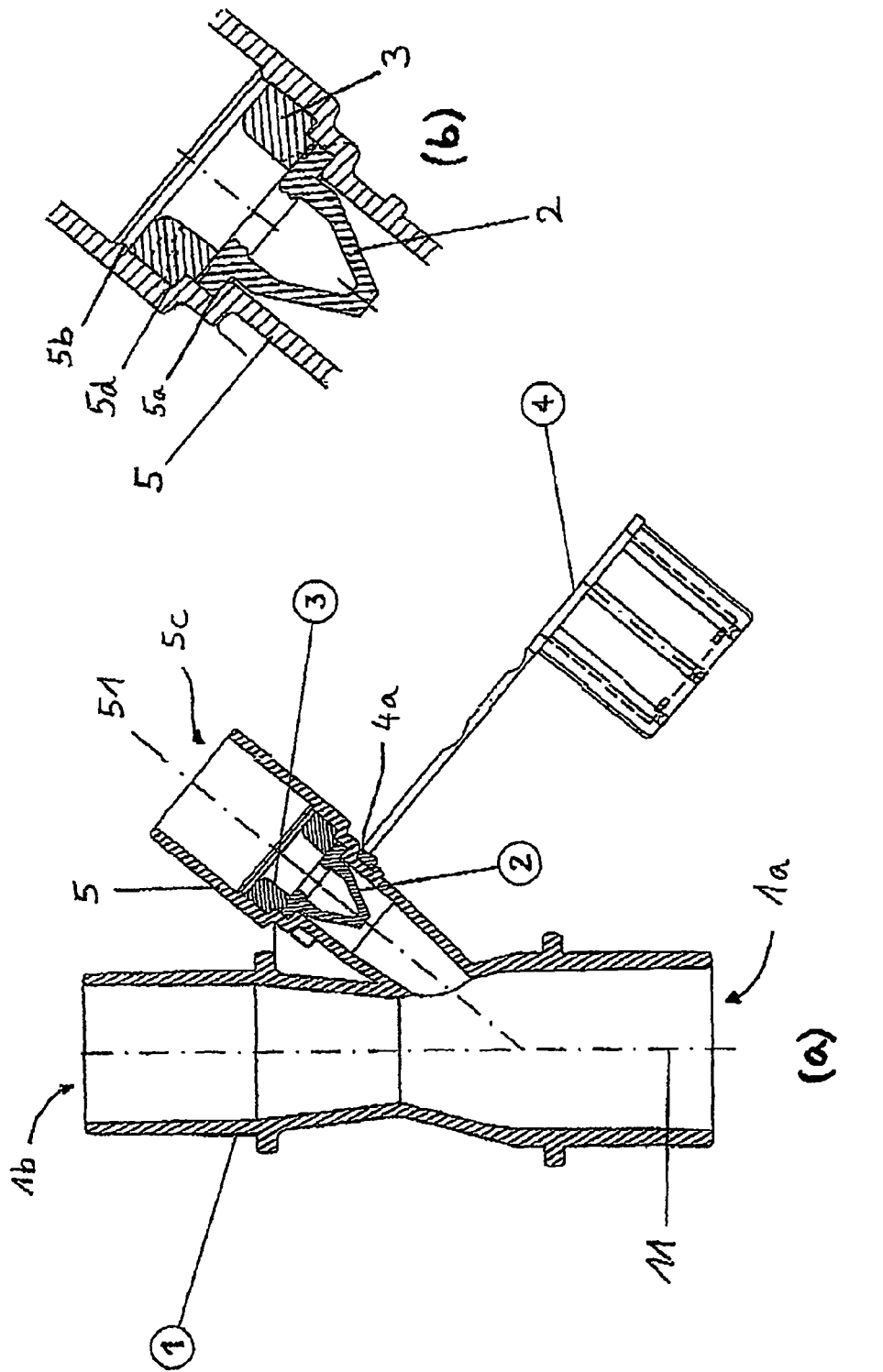
FIG. 1(a) shows a longitudinal section through a connector piece according to an embodiment of the invention.
FIG. 1(b) shows an enlarged detail of the branch, with inserted valve, from FIG. 1(a).

In FIG. 1(a), a connector piece (1) according to an embodiment of the present invention is shown in longitudinal section. The connector piece comprises a distal opening 1a for attachment to an (endo)tracheal tube (not shown), and an opposite proximal opening 1b for attachment to a ventilation and/or suction device (likewise not shown). A branch 5 protrudes laterally from the connector piece 1 and is formed integrally with the latter. The longitudinal axis 51 of the branch 5 forms an angle of 40° with the longitudinal axis 11 of the connector piece 1. The proximal end 5c of the connector piece 5 can be closed with a closure cap 4 when no catheter is inserted through the branch 5. The closure cap can, for example, be secured on the branch 5 by a loop 4a so that it cannot be mislaid when it is removed. As will be seen from FIG. 1(b), a receiving seat 5a is formed along the inner circumference of the branch 5 by means of a stepping and widening of the internal diameter, and a valve 2, for example what is called a duckbill valve, can be inserted into this receiving seat 5a. In the proximal direction from the branch, a further step 5d is formed along the inner circumference and serves as an abutment for receiving an annular cover 3. The valve can be held securely in the receiving seat 5a by means of such a cover. Farther in the proximal direction, a bead-like snap-fit lip 5b is provided along the inner circumference, and the annular cover 3 has to be pushed past this in order to snap into its position provided for fixing the valve 2. This arrangement ensures that a user always pushes the cover 3 deep enough into the receiving seat 5d, and this also prevents the cover 3 from falling out.

The valve 2 is made in one piece from an elastically deformable material, for example silicone, and its walls essentially define a half-enclosed hollow body. As can be seen from the mutually perpendicular longitudinal sections from FIGS. 2(a) and 2(b), a through-opening 21 is provided at the proximal end of the valve and a catheter can be inserted through this through-opening 21 and through the valve. Two substantially bell-shaped sealing lips 25 are formed annularly on the inner wall of the through-opening 21, these sealing lips 25 narrowing the actual diameter to the value D, which is 0.1 to 0.15 mm smaller than the nominal external diameter of the catheter.

The following dimensions are based on a nominal external diameter of the catheter of 3.25 mm. In this case, the diameter of the inner wall without sealing lips is 3.7 mm, while D=3.1 mm. The sealing lips 25 themselves have radii of curvature of R1=R1'=0.25 mm. It is also possible for the radii of curvature R1 and R1' to be chosen different than one another. Between the two sealing lips, a "valley" is arranged whose radius of curvature R2=0.1 mm. At the location where the distal sealing lip merges back into the inner wall of the valve, the associated radius of curvature is R3=0.3 mm.

In the distal direction, the opening 21 is adjoined by the beak section 22. The latter has a substantially cylindrical basic shape which, in the direction towards the beak tip 23, narrows in a wedge formation via two flats 27a and 27b lying opposite one another. Each flat forms an angle of α=27.1° with a straight line lying in the longitudinal direction of the valve. The beak tip itself is flattened, although it can also narrow to a point. In the beak tip, and parallel to an imaginary intersecting line of the two flats 27a and 27b, a slit 24 is formed which is cut into the beak tip after forming of the valve (e.g. by injection moulding). In the normal state, without inserted catheter, the slit is closed and, by virtue of the elastic material, seals the valve off against passage of fluid. The length of the slit is substantially identical to the (unconstricted) internal wall diameter of the valve 2, in other words, in the present illustrative embodiment, is 3.7 mm. Upon insertion of a catheter, the tip of the latter comes into contact with the inner faces of the wedge-shaped flats 27a and 27b and bends these out in such a way that the slit 24 opens like a mouth and the catheter can be guided through.

Figure 2:
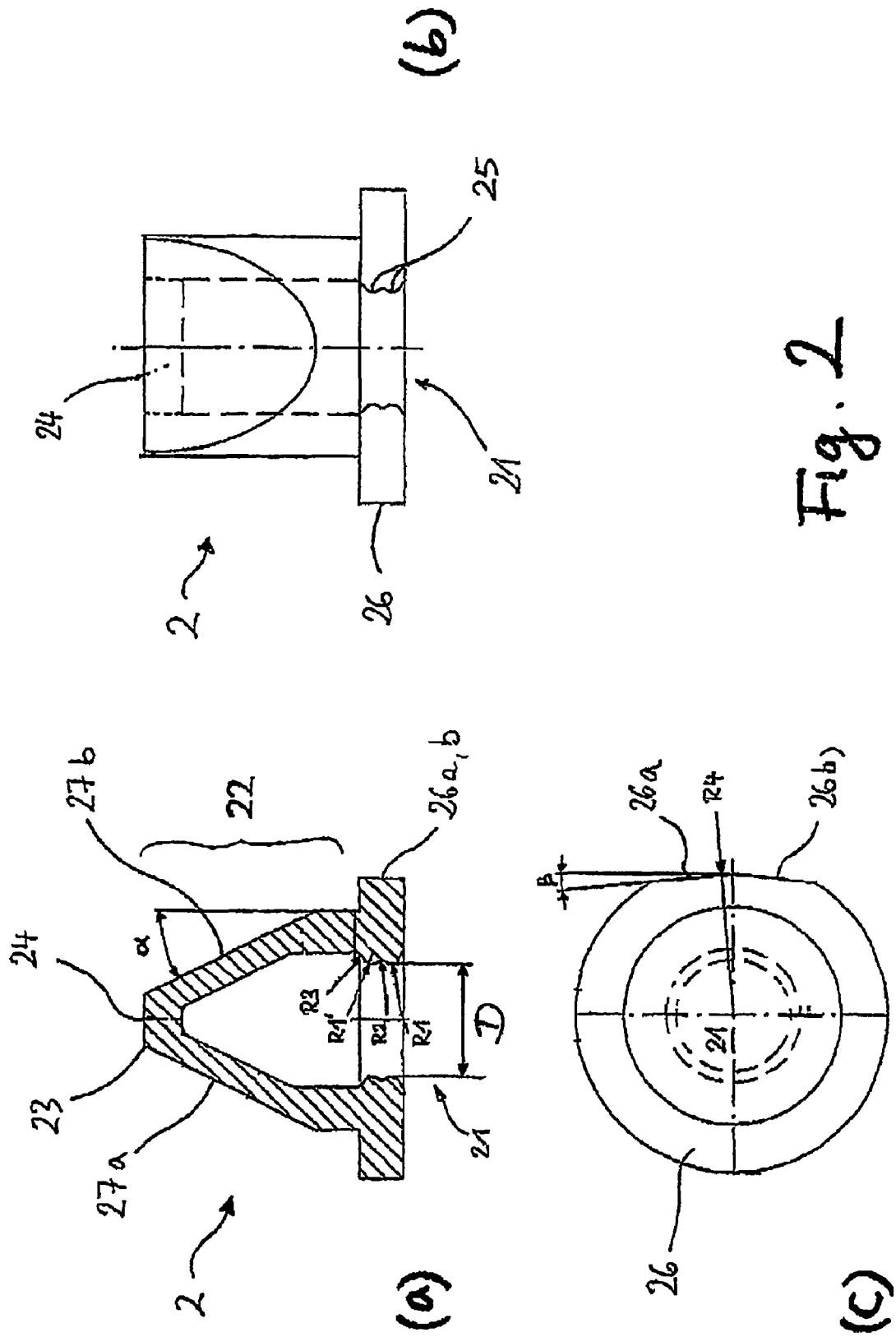
FIG. 2(a) shows a longitudinal section through a valve according to the invention.
FIG. 2(b) shows a longitudinal section through the valve perpendicular to the plane of the section in FIG. 2(a).

As can be seen from FIGS. 2(b) and 2(c), a peripheral flange 26 is formed on the outside of the valve, at its proximal end. When the valve 2 is fitted into the branch 5, this flange 26 abuts the receiving seat 5a (step of the internal diameter of the branch) and thus serves to position the valve 2. In addition, a section of the circumference of the flange is characterized by flats 26a, 26b which reduce the effective radius of the otherwise circular flange. The flats 26a, 26b of this section form an angle $\beta=6°$ with the tangent line at the centre of the section. The point of intersection of the flat (the centre of the section) is rounded and has a radius of curvature of R4=3.9 mm. The flange radius passing through the centre is perpendicular to the orientation of the slit 24 in the beak tip. In this way it is possible, using the flats 26a, 26b, to fit the valve 2 with the slit 24 into a corresponding receiving seat and to do this with controlled orientation.

Figure 3:
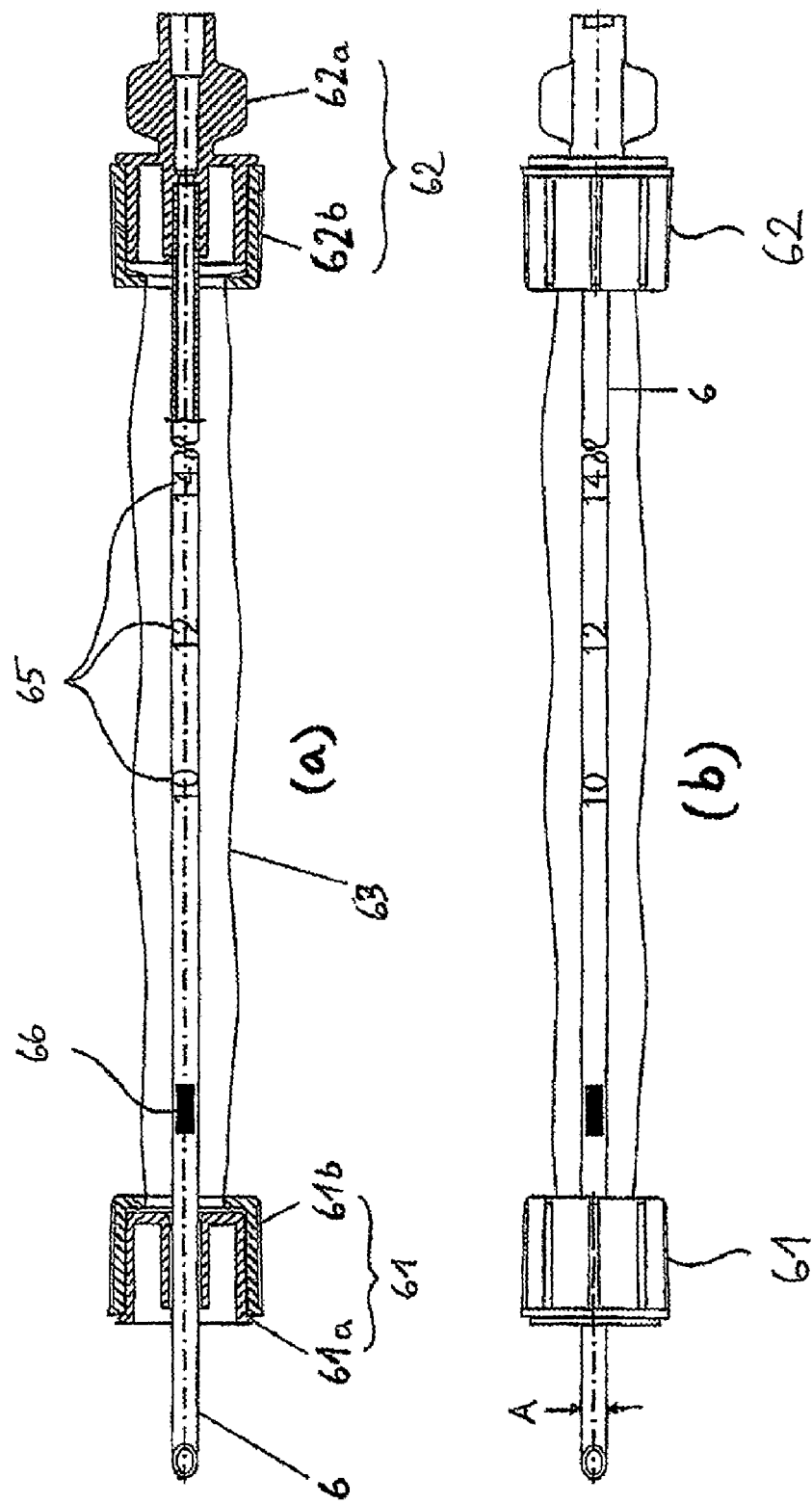
FIG. 3(a) shows a longitudinal section through a catheter according to the embodiment of the invention.
FIG. 3(b) shows a side view of the catheter.
Figure 4:
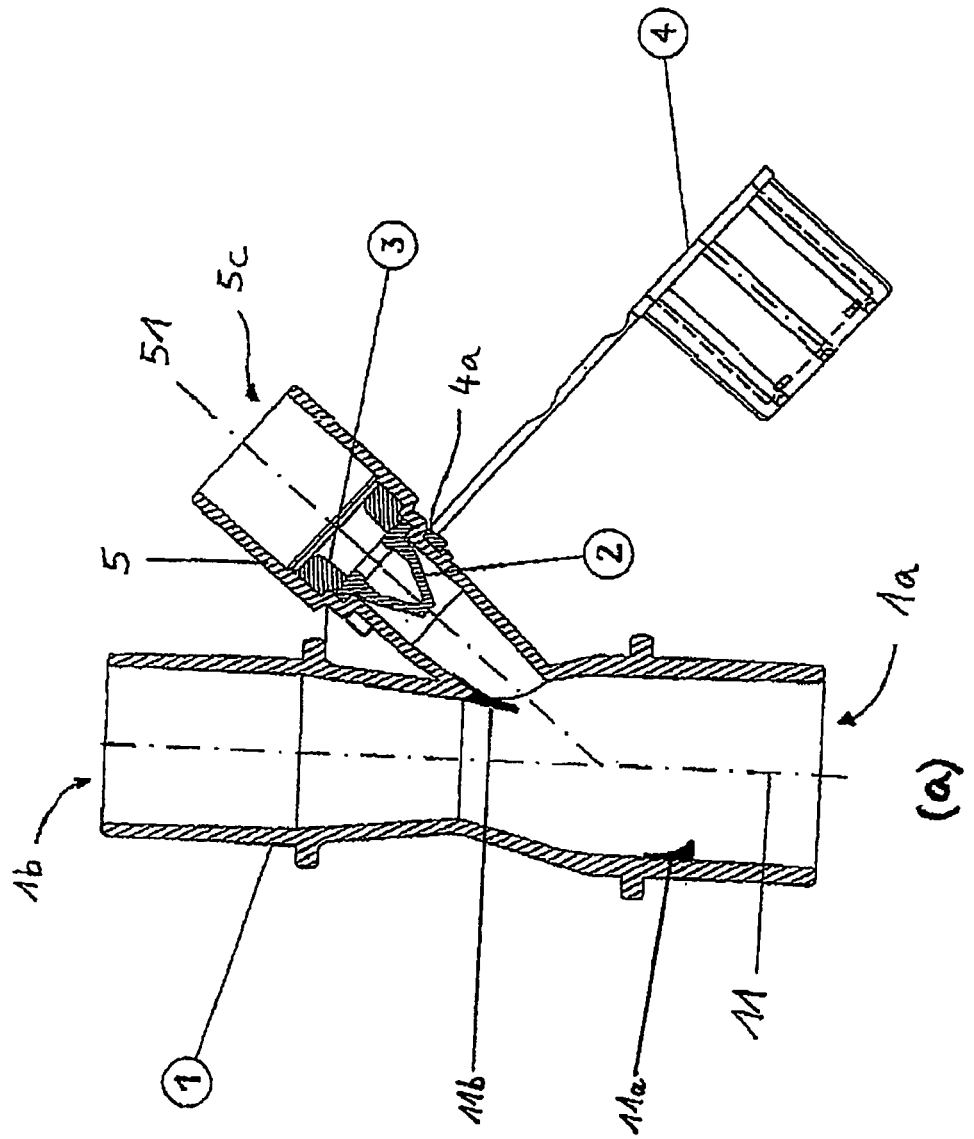
FIG. 4 shows shows a longitudinal section through a connector piece according to an embodiment of the invention with one flange and guiding lips 11a and 11b.
Figure 5:
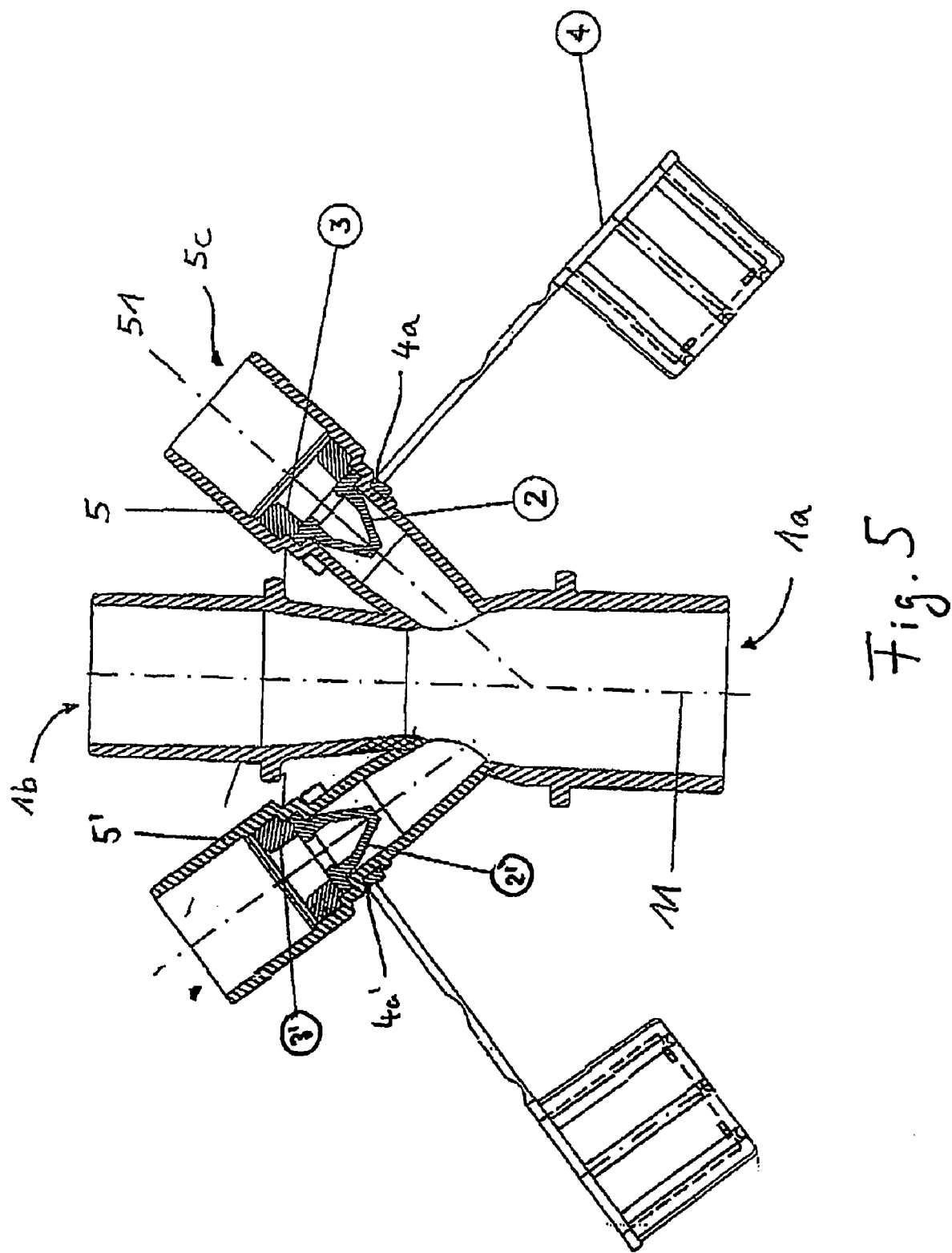
FIG. 5 shows a longitudinal section through a connector piece according to an embodiment of the invention with two flanges
Figure 6:
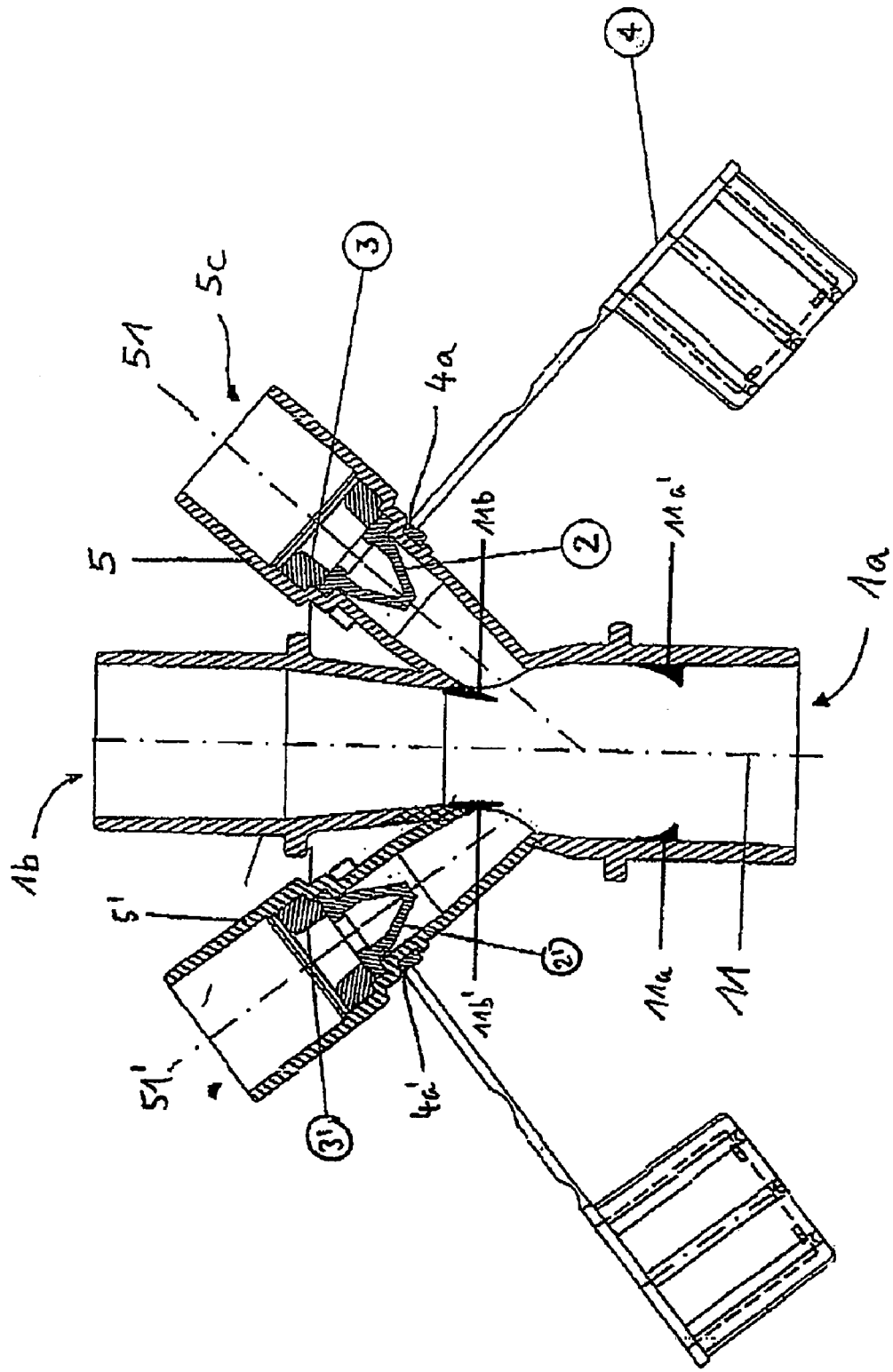
FIG. 6 shows a longitudinal section through a connector piece according to an embodiment of the invention with two flanges and guiding lips 11a and 11b and 11a' and 11b'.

Finally, in FIGS. 3(a) and 3(b), the catheter 6 itself is shown. It is guided through openings in the closure caps 61 and 62 which, distally, serve for attachment to the branch 5 of the connector piece 1 and, proximally, for attachment to the drug supply line with lung surfactant preparations. The catheter 6 is surrounded by a protective sleeve 63 which is secured on the connection caps 61 and 62 by being clamped and bonded in the space between the cap inner part 61a and the cap outer part 61b, or between the Luer connector 62a and the cap outer part 62b. Along its length, the catheter 6 has markings 65 which give a visual indication of the depth of insertion of the catheter into the patient's body.

Moreover, near the distal end of the catheter 6, a radiopaque marker 66 is provided which permits positioning of the catheter tip in the patient's body under real-time X-ray imaging.

The skilled person will doubtless be able to see further advantageous embodiments which derive from the example shown here and which also lie within the scope of this invention.

The invention claimed is:

1. An arrangement comprising an instillation catheter and a connector piece for attachment to a tracheal or endotracheal tube, the connector piece having a distal end for attachment to the tube, and a proximal end for attachment to a ventilation and/or suction device, and comprising a branch which serves for insertion of the catheter and in which a valve is arranged, the valve having a proximal through-opening and being made of an elastically deformable material configured to be opened by insertion of the catheter, characterized in that the inner wall of the proximal through-opening has a seal arranged in a circumferential direction on the inner wall preventing axial flow of fluid between catheter and inner wall, and in that, in the distal direction from the through-opening, the valve has a beak section which, at its beak tip, has a normally closed slit, wherein the seal exerts, on the outer wall of the catheter, a pressure which permits gas-tight and water-tight enclosure.

2. The arrangement according to claim 1, in which, between a distal connection cap for attachment to the branch and a proximal connection cap provided at the proximal end area of the catheter, said catheter has a protective film enclosing the catheter.

3. The arrangement according to claim 1, in which the catheter has, along its length, markings which show the user the position of the distal end of the catheter relative to the tube.

4. The arrangement according to claim 1, in which the catheter has a radiopaque indicator near the distal end.

5. The arrangement according to claim 1, in which the angle formed by the longitudinal axis of the branch and a longitudinal axis passing through the distal end of the connector piece is between 35° and 45°.

6. A one-piece valve of an elastically deformable material, which has a proximal through-opening, the valve configured to be opened by insertion of a catheter, characterized in that the inner wall of the proximal through-opening of the valve has a seal arranged in a circumferential direction on the inner wall preventing axial flow of fluid between catheter and inner wall, and in that, in the distal direction from the through-opening, the valve has a beak section which, at its beak tip, has a normally closed slit, wherein the seal exerts, on the outer wall of the catheter, a pressure which permits gas-tight and water-tight enclosure.

7. The arrangement according to claim 1, in which the internal diameter defined by the seal is between 0.05 mm and 0.2 mm smaller than the external diameter of the catheter.

8. The arrangement according to claim 1, in which the through-opening has an outer wall with a flange which serves as a sealing abutment for positioning the valve in a receiving seat of the branch.

9. The arrangement according to claim 8, in which the flange has a section defined by two lateral flats, the flats intersecting at the centre of the section.

10. The arrangement according to claim 1, in which the seal comprises a sealing lip which is arranged in the circumferential direction on the inner wall.

11. The arrangement according to claim 1, in which the seal comprises two sealing lips which are arranged in the circumferential direction on the inner wall.

12. The arrangement according to claim 10, in which the sealing lip has a substantially bell-shaped cross section.

13. The arrangement according to claim 12, in which the radius of curvature of the sealing lip is at most 0.25 mm.

14. The arrangement according to claim 11, in which a connecting area between the sealing lips is curved with a radius of curvature of at most 0.1 mm.

15. The arrangement according to claim 12, in which the valve, in the transition between the beak section and the adjoining sealing lip, is curved with a radius of curvature of at most 0.3 mm.

16. The arrangement according to claim 1, in which the beak section, starting from a cylindrical basic shape, narrows in a wedge formation via flats lying opposite one another.

17. The arrangement according to claim 1, in which an angle between the longitudinal direction of the valve and each of the two flats of the beak section is between approximately 26° and approximately 28°.

18. The arrangement according to claim 1, in which the valve can be fixed by an annular cover in the branch.

19. The arrangement according to claim 1, in which the receiving seat has a snap-fit lip for snapping the annular lid securely in place.

20. An arrangement comprising an instillation catheter and a connector piece for attachment to a tracheal or endotracheal tube, the connector piece having a distal end for attachment to the tube, and a proximal end for attachment to a ventilation and/or suction device, and comprising a branch which serves for insertion of the catheter and in which a valve is arranged, the valve having a proximal through-opening and being made of an elastically deformable material configured to be opened by insertion of the catheter, characterized in that the inner wall of the proximal through-opening has a seal preventing axial flow of fluid between catheter and inner wall, and in that, in the distal direction from the through-opening, the valve has a beak section which, at its beak tip, has a normally closed slit, wherein the seal comprises two sealing lips which are arranged in the circumferential direction on the inner wall.

* * * * *